(12) United States Patent
Yamamoto

(10) Patent No.: US 8,327,904 B2
(45) Date of Patent: Dec. 11, 2012

(54) MANUFACTURING APPARATUS OF ABSORBENT ARTICLE AND MANUFACTURING METHOD OF ABSORBENT ARTICLE

(75) Inventor: Hiroki Yamamoto, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 246 days.

(21) Appl. No.: 12/390,054

(22) Filed: Feb. 20, 2009

(65) Prior Publication Data

US 2010/0122766 A1 May 20, 2010

(30) Foreign Application Priority Data

Nov. 14, 2008 (JP) ................. P2008-292369

(51) Int. Cl.
*B32B 37/12* (2006.01)
(52) U.S. Cl. ........ 156/563; 156/199; 156/200; 156/201; 156/264; 156/265; 156/566; 156/567; 156/568; 156/552
(58) Field of Classification Search .................. 156/563, 156/199, 200, 201, 264, 265, 566, 567, 568, 156/522
See application file for complete search history.

(56) References Cited

U.S. PATENT DOCUMENTS

| | | | |
|---|---|---|---|
| 3,147,166 A * | 9/1964 | Friday | 156/264 |
| 6,497,032 B2 * | 12/2002 | Maxton et al. | 29/429 |
| 6,648,122 B1 | 11/2003 | Hirsch et al. | |
| 6,656,312 B1 | 12/2003 | Schmitz et al. | |
| 2002/0125105 A1 * | 9/2002 | Nakakado | 198/471.1 |
| 2003/0205312 A1 * | 11/2003 | Tomsovic et al. | 156/227 |
| 2007/0193856 A1 | 8/2007 | McCabe | |

FOREIGN PATENT DOCUMENTS

| | | |
|---|---|---|
| JP | 2005-298193 A | 10/2005 |
| JP | 2005298194 A * | 10/2005 |

OTHER PUBLICATIONS

Extended European Search Report for Application No. 09826156.3 mailed Mar. 21, 2012.

* cited by examiner

*Primary Examiner* — Khanh P Nguyen
*Assistant Examiner* — Margaret Squalls
(74) *Attorney, Agent, or Firm* — Lowe Hauptman Ham & Berner, LLP

(57) ABSTRACT

A work conveying mechanism according to the present invention includes a rotation drum in which an adsorbing pad for adsorbing an absorber is provided. The work conveying mechanism rotates the rotation drum and arranges the absorber on a third web being conveyed. In an outer shape of the work adsorbed by the adsorbing pad, an outer edge portion thereof is closer to a shaft center side of the rotation drum than a central portion thereof is. A work conveying mechanism includes a roller mechanism provided on a side of the third web opposite to the rotation drum side and configured to locate the third web on the adsorbing pad side. At a passing point, the roller mechanism arranges an outer edge portion of the third web in a width direction on a shaft center side of the rotation drum closer than a central portion thereof is.

10 Claims, 11 Drawing Sheets

MANUFACTURING APPARATUS OF ABSORBENT ARTICLE AND MANUFACTURING METHOD OF ABSORBENT ARTICLE

RELATED APPLICATIONS

The present application is based on, and claims priority from, Japanese Application Number 2008-292369, filed Nov. 14, 2008, the disclosure of which is hereby incorporated by reference herein in its entirety.

BACKGROUND OF THE INVENTION

1. Field of the Invention

The present invention relates to a manufacturing apparatus of an absorbent article and a manufacturing method of an absorbent article, the apparatus provided with a rotation drum including an adsorbing part that adsorbs a work, which is a component forming a part of the absorbent article.

2. Description of the Related Art

Conventionally, in a manufacturing process of absorbent articles such as disposable diapers, widely used is a manufacturing apparatus of an absorbent article including a work conveying mechanism In the work conveying mechanism, a band-like body formed of successive works, each of which is a component of an absorbent article, is cut into absorbent sheets. The work is specifically an absorbent sheet that absorbs liquid excreted from a target wearing the article (for example, a human body). In addition, the work conveying mechanism rotates an arrangement direction of the absorbent sheet by 90 degrees (for example, see Japanese Patent Application Publication No. 2005-298193 (pp. 6-7, FIG. 1)).

Such a work conveying mechanism includes a rotation drum and multiple adsorbing pads (adsorbing parts) provided on an outer circumference of the rotation drum. The adsorbing pads adsorb the cut absorbent sheets one by one. Then, by the rotation drum, the adsorbed absorbent sheets are sequentially conveyed to above a web on which continuous components of absorbent articles, for example, a back sheet arranged on the outer surfaces of the absorbent sheets and an outer sheet arranged on the outer surface of the back sheet are placed. Each absorbent sheet conveyed to above the web is arranged in a predetermined position of the web conveyed by a conveyor or the like.

For the sake of manufacturing convenience, the band-like body formed of the successive absorbent sheets is manufactured so that a longitudinal direction of each absorbent sheet would be aligned in a longitudinal direction of the band-like body, i.e., a conveyance direction of the band-like body (Machine Direction (MD)). On the other hand, as for the web, employed is a method of arranging each absorbent sheet so that the longitudinal direction of the absorbent sheet is aligned in a cross direction (CD) approximately perpendicular to the conveyance direction of the web. For this reason, the adsorbing pad is rotated by 90 degrees by rotating mechanism included in the rotation drum while being conveyed to above the web by the rotation drum.

Preferably, in order to control different circumferential velocity in the adsorbing pad when the adsorbing pad receives the absorbent sheet, the adsorbing pad, which is provided on an outer circumference of the rotation drum and thereby rotates, preferably receives the absorbent sheet while maintaining a distance of its adsorbing face from the shaft center of the rotation drum as constant as possible. For this reason, the adsorbing face is formed to have a shape in which at least its outer edge portions are inclined toward a shaft center side of the rotation drum, compared with a central portion of the adsorbing face.

However, the above-mentioned conventional manufacturing apparatus of the absorbent article has the following problems. Specifically, since the adsorbing face of the adsorbing pad is formed into the shape in which its outer edge portions are inclined toward the shaft center side of the rotation drum, problems arise such that wrinkles would appear in the absorbent sheet and the absorbent sheet deviates from the predetermined position on the web. This is because, when the adsorbing pad passes the absorbent sheet to the web with an adhesive applied thereon, the absorbent sheet adsorbed by the central portion of the adsorbing face firmly adheres to the web, while the absorbent sheet adsorbed by each outer edge portion is difficult to adhere firmly to the web.

In addition, even when the adsorbing face of the adsorbing pad is formed to have a planar shape, a thickness of the absorbent sheet is changed in some cases and the central portion of the absorbent sheet is therefore thickened. In this case, since the absorbent sheet adsorbed by each outer edge portion is difficult to adhere firmly to the web, similar to the above-mentioned, problems arise such that wrinkles occur in the absorbent sheet and the absorbent sheet deviates from the predetermined position on the web.

SUMMARY OF THE INVENTION

Then, the present invention has been made in light of such a situation. An object of the present invention is to provide a manufacturing apparatus of an absorbent article and a manufacturing method of an absorbent article in which generation of wrinkles and poor transfer can be prevented so that a work such as an absorbent sheet can adhere to a web more securely when the work is to adhere to the web under conveyance.

In order to solve tasks mentioned above, the present invention has the following aspects. First, a first aspect of the present invention is summarized as a manufacturing apparatus (work conveying mechanism 100) of an absorbent article wherein, a rotation drum (rotation drum 102) provided with an absorbing part (absorbing pad 110) for absorbing a work (absorber 4) that is a component forming a part of the absorbent article (absorbent article 1), at a receiving point (receiving point P1) of the work, for changing an arrangement direction of the work from a first arrangement direction (first arrangement direction D1) of the work to a second arrangement direction (second arrangement direction D2) of the work at a passing point (passing point P2) of the work onto a web (third web 7C) while the rotation drum is rotating, and for arranging the work adsorbed by the adsorbing part on the conveyed web on which continuous components of the absorbent article are placed, the manufacturing apparatus comprising: a web position guiding mechanism (for example, roller mechanism 120) provided on the opposite side of the web from a side on which the rotation drum is located, and configured to locate the web on an adsorbing part wherein in a cross section of the adsorbing part taken along the second arrangement direction at the passing point, the work adsorbed by the adsorbing part has an outer shape and an outer edge portion of the work is closer to a shaft center of the rotation drum than a central portion of the work and, in a width direction of the web perpendicular to a conveyance direction of the web at the passing point, the web position guiding mechanism arranges a width-direction outer edge portion of the web, which is a part corresponding to the outer edge portion of the work at the passing point P2, to be closer to the shaft center of the rotation drum than the width-direction central portion of the web is.

Such a web position guiding mechanism locates the web so that, the outer edge portion in the width direction of the web may be brought closer to the adsorbing part than the central portion of the web in the width direction is, and therefore, the web can be adhered to the work so as to correspond to the shape of the work.

Accordingly, when causing the work to adhere to the web under conveyance, the manufacturing apparatus of the absorbent article can prevent generation of wrinkles and poor transfer, and can cause the work to adhere to the web more securely.

A second aspect of the present invention is summarized in that according to the first aspect of the present invention, in a cross section taken along the first arrangement direction of the adsorbing part at a receiving point, a central portion (central portion 116) of an adsorbing face (adsorbing face 112) of the adsorbing part is formed to be closer to the shaft center of the rotation drum than an outer edge portion (end 114 and end 118) of the adsorbing face is.

A third aspect of the present invention is summarized in that according to the first or second aspect of the present invention, the web position guiding mechanism is a roller mechanism (for example, roller mechanism 120) that is rotatable in the conveyance direction (conveyance direction MD) of the web, the roller mechanism includes an outer side roller (for example, outer side roller 122 and outer side roller 124) provided in a position corresponding to the outer edge portion of the adsorbing part in a state of being aligned in the second arrangement direction, and an outer circumferential surface of the outer side roller is approximately parallel to a line along the outer edge portion of the adsorbing face.

A fourth aspect of the present invention is summarized in that according to the third aspect of the present invention, the outer side roller has a shaft center approximately parallel to the width direction of the web, and gradually increases its outer diameter toward an outer side of the web in the width direction.

A fifth aspect of the present invention is summarized in that according to the third aspect of the present invention, the outer side roller (for example, outer side roller 128 and outer side roller 130) has a shaft center approximately parallel to the line along the outer edge portion of the adsorbing face.

A sixth aspect of the present invention is summarized in that according to the fourth or fifth aspect of the present invention, the roller mechanism includes a central roller (for example, central roller 132) that is provided in a position corresponding to the central portion of the adsorbing part and has a shaft center approximately parallel to the width direction of the web, and the outer side roller is provided on an outer side of the central roller in the width direction of the web.

A seventh aspect of the present invention is summarized in that according to the sixth aspect of the present invention, the shaft center of the central roller and the shaft center of the outer side roller are independent of each other.

An eighth aspect of the present invention is summarized in that according to any one of the third aspect through the seventh aspect of the present invention, the roller used for the roller mechanism is formed of an elastic member.

A ninth aspect of the present invention is summarized in that according to the second aspect of the present invention, the web position guiding mechanism (web position guiding mechanism 120D) includes a support member (support member 132A and support member 132B) that supports the width-direction outer edge portion of the web, and in a view point from an extending direction of the shaft center of the rotation drum, the support member is provided closer to the rotation drum than a tangent of a rotation trajectory of the center of the adsorbing face at the passing point is.

A tenth aspect of the present invention is summarized as a manufacturing method of an absorbent article, by using a rotation drum (rotation drum 102) provided with an adsorbing part (adsorbing pad 110) for adsorbing a work (absorber 4) that is a component forming a part of the absorbent article (absorbent article 1), for changing arrangement direction of the work from a first arrangement direction (first arrangement direction D1) of the work to a second arrangement direction (second arrangement direction D2) of the work at a passing point (passing point P2) of the work onto a web (third web 7C) while the rotation drum is rotated, and for arranging the work adsorbed by the adsorbing part on a conveyed web on which continuous components of the absorbent article are placed, and a web position guiding mechanism (for example, roller mechanism 120) provided on the opposite side of the web from a side on which the rotation drum is located, and configured to locate the web on an adsorbing part. The method including a web position guide process to locate the web on an adsorbing part at the passing point, the work adsorbed by the adsorbing part has an outer shape and an outer edge portion of the work is closer to a shaft center of the rotation drum than the central portion of the work, and in a width direction of the web perpendicular to a conveyance direction of the web, the web position guiding mechanism arranges an outer edge portion of the web that is a part corresponding to the outer edge portion of the work closer to a shaft center of the rotation drum, than the width-direction central portion of the web is.

According to the aspects of the present invention, the manufacturing apparatus of the absorbent article and the manufacturing method of the absorbent article can be provided in which generation of wrinkles and poor transfer can be prevented and a work such as an absorbent sheet can adhere to the web more securely when the work is to adhere to the web under conveyance.

DESCRIPTION OF THE PREFERRED EMBODIMENTS

Figure 1:
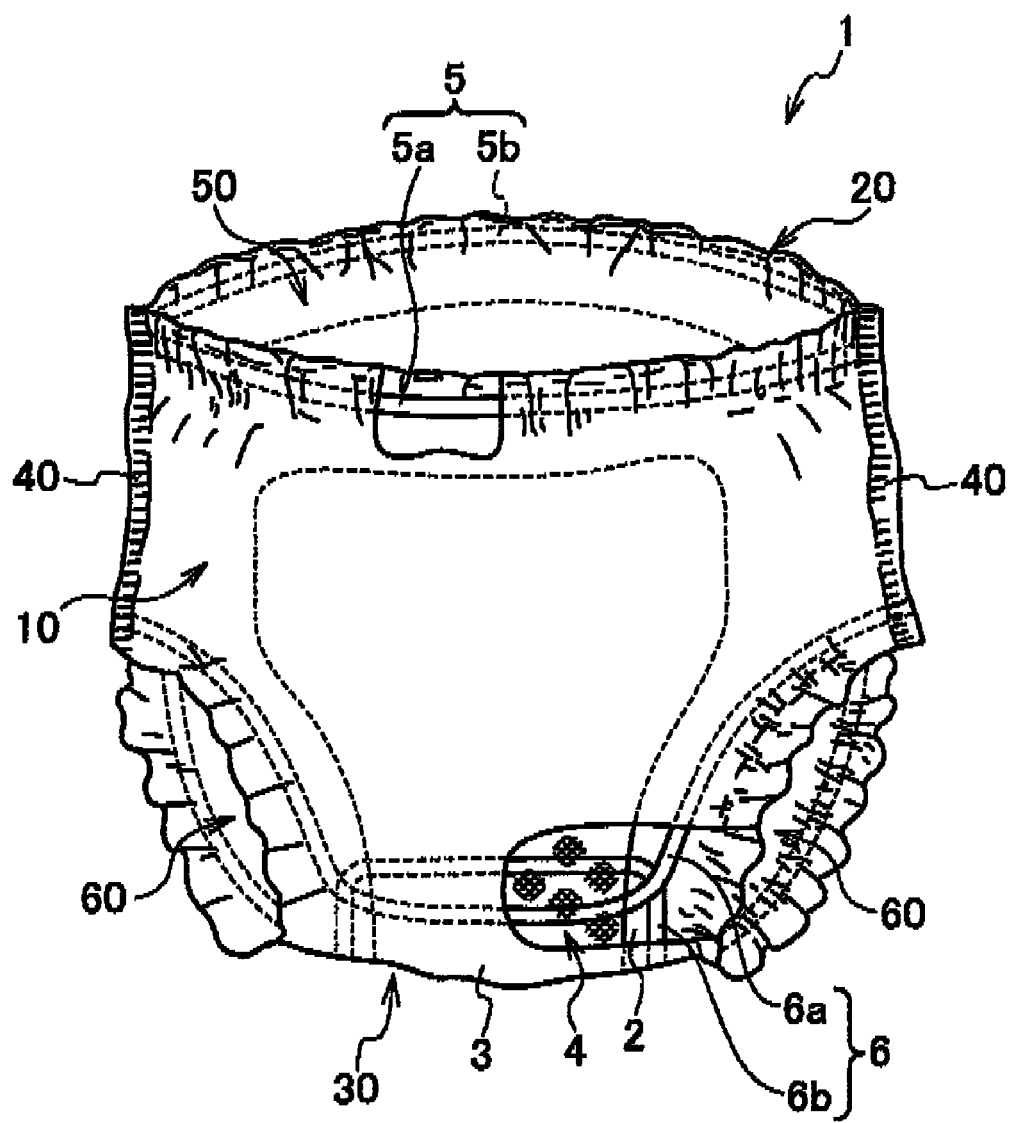
FIG. 1 is a perspective view showing an absorbent article according to a first embodiment of the present invention.

Then, description will be given of embodiments of a manufacturing apparatus of an absorbent article and a manufacturing method of an absorbent article according to the present invention, referring to the drawings. In the following description of the drawings, same or similar reference symbols are given to denote same or similar portions. However, it should be noted that the drawings are schematic and ratios of dimensions and the like are different from actual ones.

Therefore, specific dimensions and the like should be determined by taking into consideration the following description. Moreover, as a matter of course, also among the drawings, there are included portions in which dimensional relationships and ratios are different from each other.

First Embodiment

In the present embodiment, description will be given of: (1) configuration of absorbent article, (2) Manufacturing Method of Absorbent Article, (3) Entire Configuration of Manufacturing Apparatus of Absorbent Article, (4) Detailed Configuration of Web Position Guiding Mechanism, (5) Operation of Manufacturing Apparatus of Absorbent Article, (6) Advantages and Effects, and (7) Modified Example.

(1) Configuration of Absorbent Article

Firstly, a configuration of an absorbent article according to the present embodiment will be described by referring to the drawings. FIG. 1 is a perspective view showing an absorbent article according to the present embodiment. In the present embodiment, an absorbent article 1 is a disposable diaper for adults.

As shown in FIG. 1, the absorbent article 1 is mainly formed of a liquid permeable front sheet 2 which comes in contact with a skin of a target wearing the article (hereinafter, a wearer), a liquid impermeable back sheet 3 provided at the outer side of the front sheet 2, and an absorber 4 which is provided between the front sheet 2 and the back sheet 3, and absorbs dejecta from the wearer.

In addition, a liquid impermeable waterproof sheet (unillustrated) is provided between the back sheet 3 and the absorber 4. That is, the absorber 4 is provided between the front sheet 2 and the waterproof sheet.

As the front sheet 2, employed is a nonwoven fabric, a perforated plastic film, or the like. As the back sheet 3, employed is a nonwoven fabric. As the absorber 4, employed is ground pulp, a mixture of ground pulp and high absorbent polymer particles, or the like.

The absorbent article 1 has a front waistline region 10 corresponding to a front waistline of the wearer, a back leg circumference portion 20 corresponding to a back waistline of the wearer, and a crotch portion 30 corresponding to a crotch of the wearer.

The front waistline region 10 and the back leg circumference portion 20 are integrated by connecting portions 40. A waist gather 5 made of an elastic rubber or the like is provided at the peripheries of the front waistline region 10 and the back leg circumference portion 20. The waist gather 5 is formed of a front waist gather 5a positioned in the front waistline region 10 and a back waist gather 5b positioned in the back leg circumference portion 20. A waistline opening 50 is formed between the front waist gather 5a and the back waistline gather 5b.

The front waistline region 10 and the back leg circumference portion 20 have stretching properties in a conveyance direction MD (MD) of a first web 7A forming the front sheet 2 and a second web 7B (see, FIG. 2) forming the back sheet 3. For example, the front waistline region 10 and the back leg circumference portion 20 may be elastic in the conveyance direction MD by providing the waist gather 5 or may be elastic in the conveyance direction MD by forming the front waistline region 10 and the back leg circumference portion 20 themselves with elastic sheets.

The crotch region 30 is provided between the front waistline region 10 and the back leg circumference portion 20. Leg gathers 6, each formed of an elastic rubber or the like, are formed on both sides of the crotch portion 30. In the vicinity of a leg opening 60, the leg gather 6 is formed of a front leg gather 6a positioned closer to the front waistline region 10 and a back leg gather 6b positioned closer to the back leg circumference portion 20. Leg circumferential opening portions 60 are formed between the front leg gather 6a and the back leg gather 6b.

The crotch portion 30 is elastic in the cross direction CD (CD) crossing the conveyance direction MD. For example, the crotch portion 30 may be elastic in the cross direction CD by providing the leg gather 6 therein or may be elastic in the cross direction CD by forming the crotch portion 30 itself with an elastic sheet.

(2) Manufacturing Method of Absorbent Article

Figure 2:
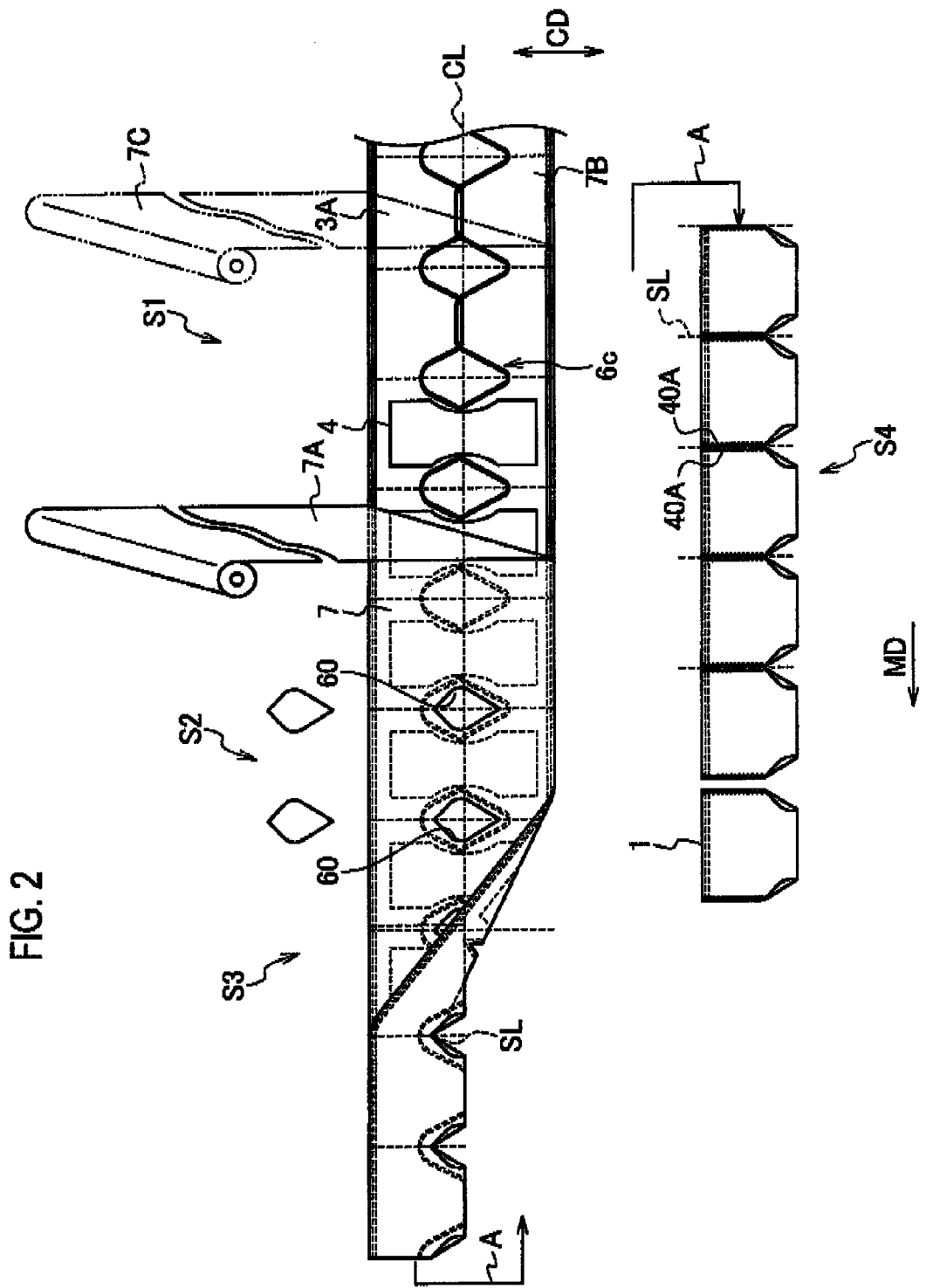
FIG. 2 is a diagram for describing a part of a manufacturing method of an absorbent article according to the first embodiment of the present invention.
Figure 3:
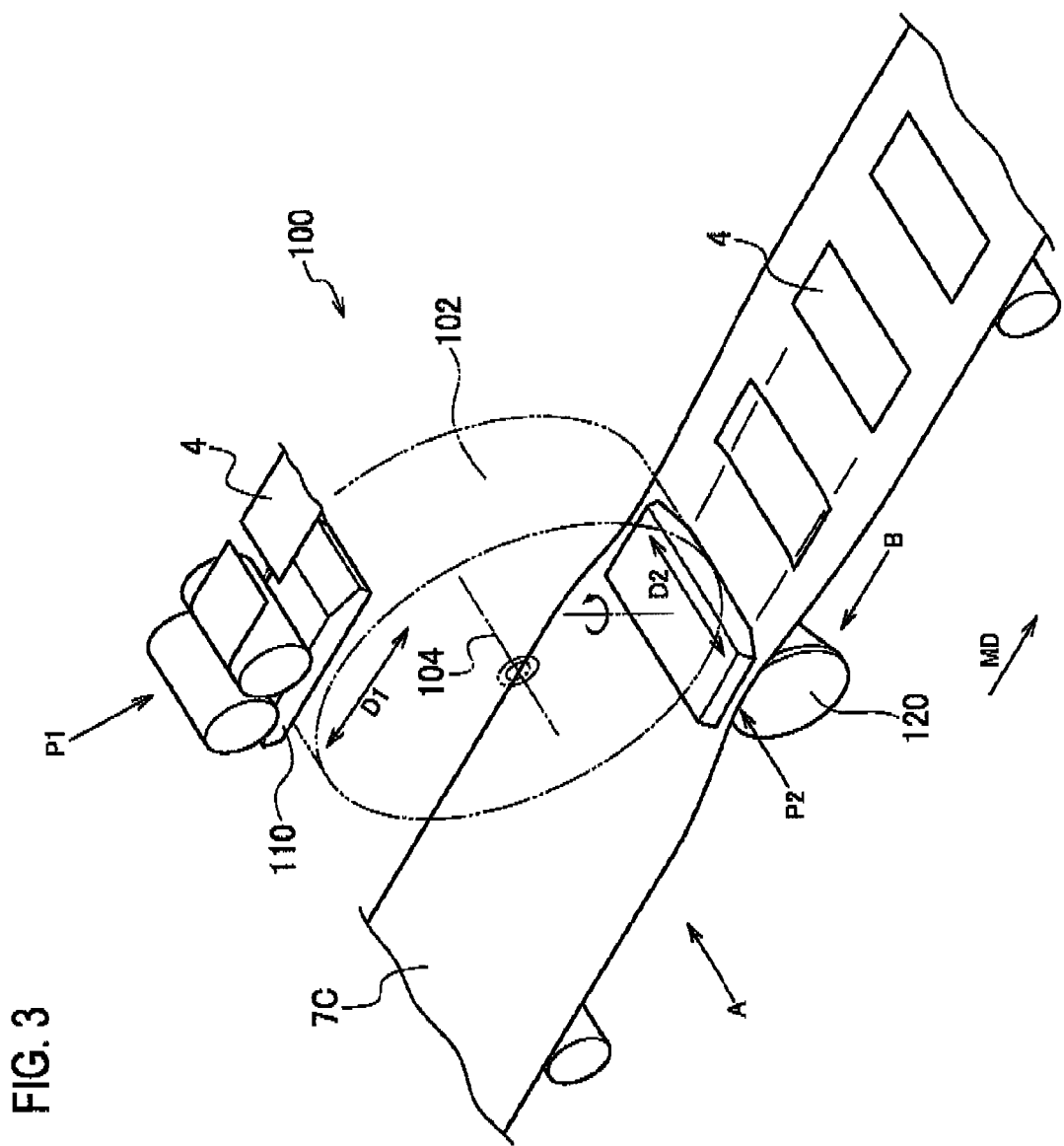
FIG. 3 is a perspective view showing an entire configuration of the manufacturing apparatus of the absorbent article according to the first embodiment of the present invention.

Next, a configuration of a manufacturing method of an absorbent article according to the present embodiment will be described by referring to the drawings. FIG. 2 is a view for illustrating a part of a manufacturing method of an absorbent article according to the present embodiment. FIG. 3 is a perspective view showing an entire configuration of a manufacturing apparatus of the absorbent article according to the present embodiment.

As shown in FIG. 2, the manufacturing method of an absorbent article includes at least a component mounting process, a leg circumference forming process, a folding process, and a cutting process. Note that processes of conveying webs in the conveyance direction MD (predetermined direction) are included between the individual processes by using an unillustrated conveyance apparatus (for example, a belt conveyance apparatus). The webs conveyed here are the liquid permeable first web 7A used to form the front sheet 2, the liquid impermeable second web 7B used to form the back sheet 3, and a third web 7C which is formed of the same material as that of the second web 7B and used to form the back sheet 3.

(2-1) Component Mounting Process

In the component mounting process S1, components constituting the absorbent article 1, such as the elastic member, the third web 7C, the waterproof sheet (unillustrated), and the absorber 4, are mounted on the second web 7B.

As shown in FIG. 3, in the component mounting process S1 according to the embodiment of the present invention, the rotation drum 102 provided with the adsorbing pad 110 (adsorbing part) rotates so that the work (absorber 4 in the present embodiment) adsorbed by the adsorbing pad 110 is arranged on the conveyed third web 7C on which the continuous components of the absorbent article 1 are placed.

Specifically, the component mounting process S1 includes at least an arrangement changing process and a web position guiding process. In the arrangement changing process, the absorber 4 is adsorbed at a receiving point of the absorber 4, and the arrangement direction of the absorber 4 is changed from the first arrangement direction of the absorber 4 to the second arrangement direction of the absorber 4 at a passing point of the absorber 4 onto the third web 7C.

In the web position guiding process, the third web 7C is arranged on the adsorbing pad 110 side by a web position guiding mechanism (to be described later) at the passing point.

(2-2) Leg Circumference Forming Process

In the leg circumference forming process S2, after the component mounting process S1, the large ring portion 6c that forms the leg gather 6 is cut out on the second web 7B and the first web 7A with the components being held therebetween (hereinafter, a composite web 7) to form the leg circumference opening part 60.

(2.3) Folding Process

In a folding process S3, after the leg circumference forming process S2, the composite web 7 is folded into halves.

(2.4) Cutting Process

In a cutting process S4, after the folding process S3, a predetermined region 40A corresponding to the connecting portion 40 of the absorbent article 1 is formed, and thereafter the composite web 7 is cut. Thereby, the absorbent article 1 is formed.

(3) Entire Configuration of Manufacturing Apparatus of Absorbent Article

Figure 4:
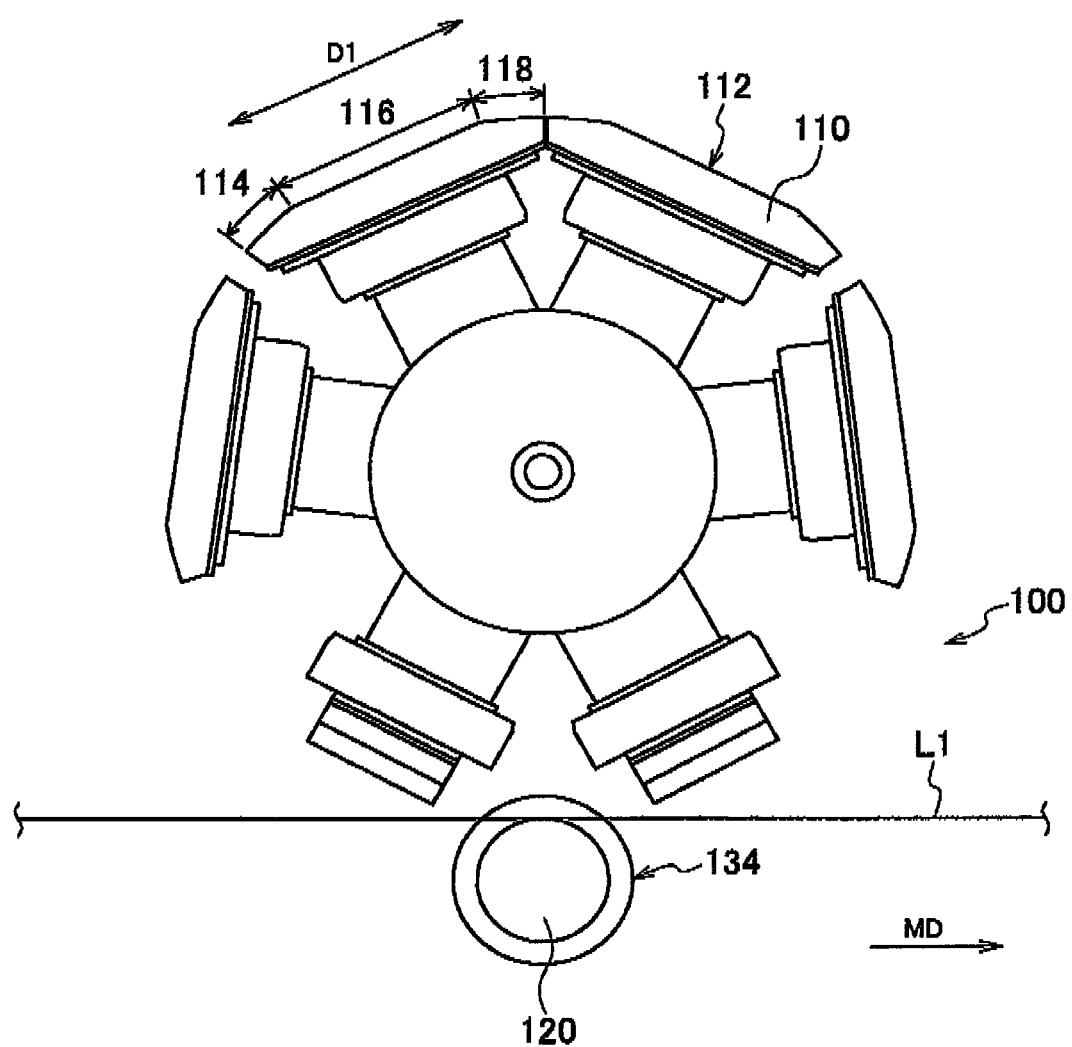
FIG. 4 is a side view (a view seen in the direction of an arrow A in FIG. 3) showing the manufacturing apparatus of the absorbent article according to the first present embodiment of the present invention.

Next, description will be given of an entire configuration of a manufacturing apparatus of an absorbent article used in the component mounting process mentioned above, referring to the drawings. FIG. 3 is a perspective view showing an entire configuration of a manufacturing apparatus of an absorbent article according to the present embodiment. FIG. 4 is a side view (a view seen in the direction of an arrow A in FIG. 3) showing the manufacturing apparatus of the absorbent article according to the present embodiment.

As shown in FIGS. 3 and 4, a work conveying mechanism 100 that forms the manufacturing apparatus of the absorbent article includes a rotation drum 102, multiple adsorbing parts (hereinafter, adsorbing pads 110) provided on an outer circumference of the rotation drum 102, and a web position guiding mechanism.

Detailed description will be given of each part that forms the work conveying mechanism 100. Specifically, description will be given of (3.1) rotation drum, (3.2) adsorbing part, and (3.3) web position guiding mechanism.

(3.1) Rotation Drum

The rotation drum 102 has the adsorbing pad 110 for adsorbing the work, which is a component that forms a part of the absorbent article 1.

The rotation drum 102 rotates around a shaft center 104. Thereby, the work (absorber 4 in the present embodiment) adsorbed by the adsorbing pad 110 is arranged on the conveyed third web 7C on which the continuous components of the absorbent article 1 are placed.

The rotation drum 102 has a rotating mechanism inside the rotation drum 102. Specifically, while conveying the adsorbing pad 110 to above the third web 7C, the rotation drum 102 rotates the adsorbing pad 110 by 90 degrees using a rotating mechanism.

(3.2) Adsorbing Part

The adsorbing pad 110 adsorbs the absorber 4, which forms a cut absorbent sheet, one by one. By the rotation drum 102, the adsorbing pad 110 is conveyed to above the third web 7C on which the continuous sheets such as the liquid impermeable waterproof sheet arranged on the outer side of the absorber 4 and the back sheet 3 arranged on the outer side of the waterproof sheet are placed.

The adsorbing pad 110 adsorbs the absorber 4. Then, while the rotation drum 102 rotates, the rotating mechanism provided inside the rotation drum 102 changes the arrangement direction at the receiving point P1 of the absorber 4 to the arrangement direction at the passing point P2 of the absorber 4.

In a cross section taken in the first arrangement direction D1 of the adsorbing pad 110 at the receiving point P1, a central portion 116 of an adsorbing face 112 of the adsorbing pad 110 is formed to be closer to a shaft center 104 of the rotation drum 102 than an outer edge portion (end 114, end 118) located on an outer side of the central portion 116 of the adsorbing face 112 is.

Additionally, the adsorbing face 112 of the adsorbing pad 110 at the passing point P2 is in a shape such that an outer edge portion (end 114, end 118) in the second arrangement direction D2 of the adsorbing face 112 is inclined toward the shaft center 104 side of the rotation drum 102.

Specifically, in a view point from an extending direction of the shaft center 104 of the rotation drum 102 at the passing point P2, the end 114 and the end 118 of the adsorbing face 112 in the second arrangement direction D2 is inclined toward the shaft center 104 side compared with the central portion 116 thereof.

The adsorbing pad 110 at the passing point P2 has the outer edge portion (end 114, end 118) of the adsorbing face 112 located closer to the shaft center 104 side of the rotation drum 102 than the central portion 116 of the adsorbing face 112 is located Moreover, the absorber 4 according to the present embodiment has a uniform thickness.

Accordingly, in a cross section of the adsorbing pad 110 taken along the second arrangement direction D2 at the passing point P2, the work adsorbed by the adsorbing pad 110 has an outer shape sand an outer edge portion located on an outer side of the central portion of the work is closer to the shaft center 104 side or the rotation drum 102 than a central portion of the work.

(3.3) Web Position Guiding Mechanism

The web position guiding mechanism is provided on a side of the third web 7C opposite to the rotation drum 102 side, and arranges the third web 7C on the adsorbing pad 110 side.

Specifically, in the present embodiment, in a width direction of the third web 7C perpendicular to the conveyance direction MD of the third web 7C at the passing point P2, the web position guiding mechanism arranges an outer edge portion of the third web 7C, which is a part corresponding to the outer edge portion of the absorber 4 at the passing point P2, closer to the shaft center 104 of the rotation drum 102 than a central portion of the third web 7C in the width direction. In other words, in the present embodiment, the web position guiding mechanism arranges the outer edge portion of the third web 7C in the width direction of the third web 7C closer to the adsorbing pad 110 than the central portion in the width direction of the third web 7C.

The outer edge portion of the third web 7C indicates a region located outer side of the central portion of the third web 7C in the width direction of the third web 7C at the passing point P2. In the present embodiment, the outer edge portion of the absorber 4 is a portion corresponding to the outer edge portion (end 114 and end 118) of the adsorbing pad 110 at the passing point P2.

The outer edge portion of the third web 7C in the width direction does not always indicate the end of the third web 7C in the width direction at the passing point P2. For example, when the third web 7C is further wider in the width direction, this means that the end of the third web 7C in the width direction may be farther from the adsorbing pad 110 than the central portion of the third web 7C in the width direction.

(4) Detailed Configuration of the Web Position Guiding Mechanism

Figure 5:
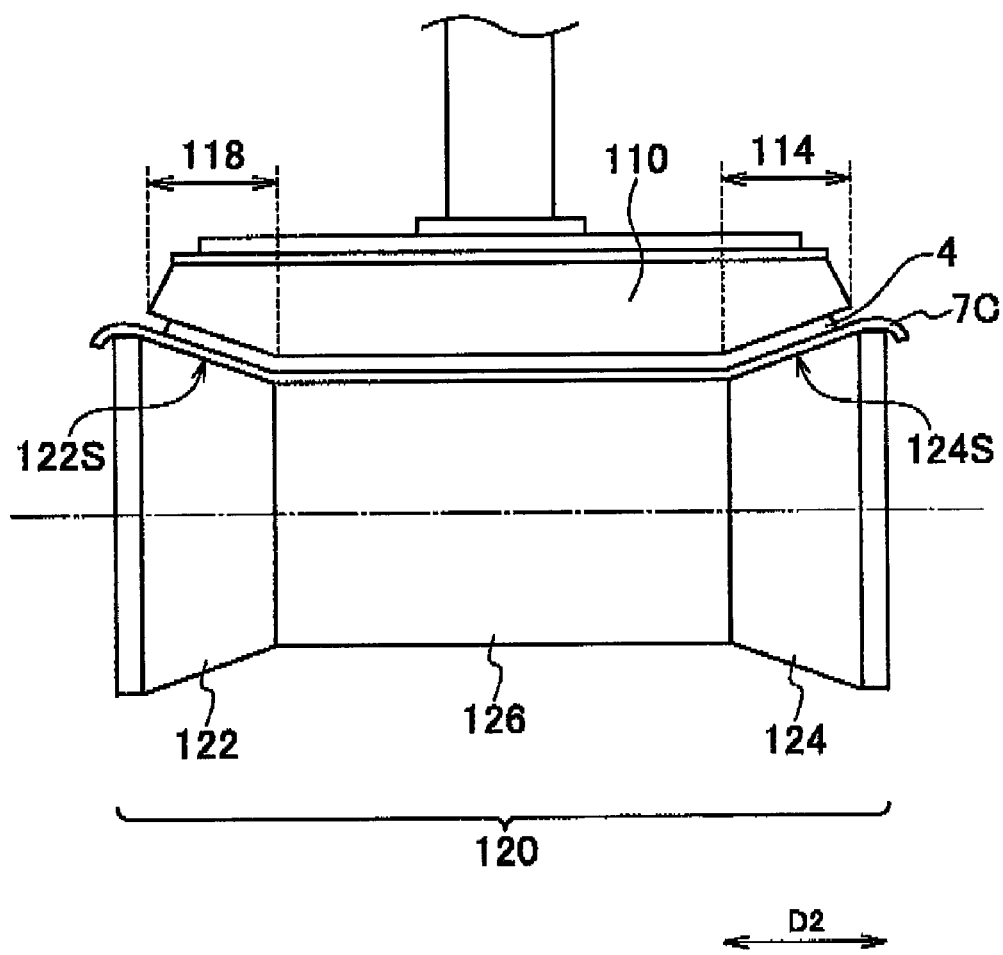
FIG. 5 is a side view (a view seen in the direction of an arrow B in FIG. 3) showing a web position guiding mechanism according to the first present embodiment of the present invention.

A detailed configuration of the web position guiding mechanism will be described using FIGS. 4 and 5. FIG. 5 is a side view (a view seen in the direction of an arrow B of FIG. 3) showing the web position guiding mechanism according to the present embodiment.

The web position guiding mechanism in the present embodiment forms a roller mechanism 120 that is rotatable in the conveyance direction MD of the second web 7B.

As shown in FIGS. 4 and 5, the roller mechanism 120 is formed of an outer side roller 122, an outer side roller 124, and a central roller 126. The roller mechanism 120 includes the outer side roller 122 and the outer side roller 124, which are provided in positions corresponding to the outer edge portions (end 118 and end 114) of the adsorbing pad 110 in the state where the adsorbing pad 110 is aligned in the second arrangement direction D2.

The roller mechanism 120 includes the central roller 126 that is provided in a position corresponding to the central portion 116 of the adsorbing pad 110 and has a shaft center approximately parallel to the width direction of the third web 7C. The outer side roller 122 and the outer side roller 124 are provided on outer sides of the central roller in the width direction of the third web 7C.

In the description below, since the outer side roller 124 has the same characteristics as those of the outer side roller 122, detailed description of the outer side roller 124 will be omitted.

A roller used for the roller mechanism 120 is formed of an elastic member. Specifically, the roller used for the roller mechanism 120 is made of a rubber made of silicon, urethane, or the like to be in a sponge-like form, a polyurethane rubber, a silicone rubber, or the like.

The roller mechanism 120 is provided downstream in the conveyance direction MD of the third web 7C from the passing point P2. A peripheral part 134 of the roller mechanism 120 is provided closer to the shaft center 104 of the rotation drum 102 than a tangent L1 to a rotation trajectory of a center of the adsorbing face 112 at the passing point P2 is, in a view point from the extending direction of the shaft center 104 of the rotation drum 102.

In a view point from the conveyance direction MD of the second web 7B, an outer circumferential surface 122S of the outer side roller 122 is approximately parallel to a line along the outer edge portion (end 118) of the adsorbing face 112. The outer side roller 122 gradually increases its outer diameter toward the outer side of the third web 7C in the width direction. The surface of the outer side roller 122 may include some projections and depressions.

(5) Operation of Manufacturing Apparatus of Absorbent Article

Next, using FIGS. 3 to 5, description will be given of operation of the manufacturing apparatus of the absorbent article according to the present embodiment (hereinafter, work conveying mechanism 100).

The absorber 4 is supplied from above the work conveying mechanism 100.

In the successive absorber 4 formed into the band-like bodies, a longitudinal direction of the absorber 4 is aligned in a longitudinal direction of the band-like body, i.e., the conveyance direction of the band-like body.

The adsorbing pad 110 adsorbs the absorber 4 at the receiving point P1 of the absorber 4.

In the present embodiment, the successive absorber 4 formed into the band-like bodies is cut in a shorter direction of the absorber 4 before being adsorbed by the adsorbing pad 110. However, the absorber 4 may be adsorbed by the adsorbing pad 110 first, and then cut in the shorter direction of the absorber 4 to be formed into the individual absorber 4.

While conveying the adsorbing pad 110 to above the third web 7C, the rotation drum 102 rotates the adsorbing pad 110 by 90 degrees. Specifically, while conveying the adsorbing pad 110 from the receiving point P1 to the passing point P2 of the absorber 4, the rotation drum 102 rotates the adsorbing pad 110 by 90 degrees using the rotating mechanism provided inside the rotation drum 102.

In this way, the adsorbing pad 110 changes the arrangement direction of the absorber 4 from the first arrangement direction D1 of the absorber 4 to the second arrangement direction D2 of the absorber 4.

The adsorbing pad 110 passes the absorber 4 to the third web 7C, to which an adhesive is applied, at the passing point P2 of the absorber 4.

Specifically, at the passing point P2 of the absorber 4, the adsorbing pad 110 releases attachment of the absorber 4, to detach the absorber 4.

The roller mechanism 120 locates the third web 7C on the adsorbing pad 110 side at the passing point P2. Specifically, the roller mechanism 120 arranges an outer edge portion (the third web 7C corresponding to an outer circumferential surface 122S and an outer circumference S124S) in the width direction of the third web 7C closer to the shaft center of the rotation drum 102 than the central portion of the third web 7C in the width direction is, to locate the third web 7C.

Thereby, the absorber 4 is arranged on the third web 7C being conveyed.

(6) Advantages and Effects

As described above, according to the present embodiment, the outer shape of the work adsorbed by the adsorbing pad 110 is determined by matching a thickness of the absorber 4 with a thickness (shape) of the adsorbing face 112. As for an outer diameter of the work at the passing point P2, the outer edge portion of the work is closer to the shaft center 104 of the rotation drum 102 than the central portion of the work. In other words, a distance from the third web 7C to the central portion of the work is shorter than a distance from the third web 7C to the outer edge portion of the work.

On the other hand, the web position guiding mechanism locates the third web 7C in such a way as to bring the outer edge portion of the third web 7C in the width direction closer to the adsorbing pad 110 than the central portion of the third web 7C in the width direction, Accordingly, the web position guiding mechanism can cause the third web 7C to be adhered to the absorber 4 in accordance with the shape of the absorber 4, and the roller mechanism 120 can steadily locate the third web 7C on the adsorbing pad 110 side at the passing point P2.

Consequently, when the work such as the absorber 4 is to adhere on the third web 7C being conveyed, the work conveying mechanism 100 can cause the work to adhere to the web more securely while preventing generation of wrinkles and poor transfer.

According to the present embodiment, since being the roller mechanism (roller mechanism 120) that is rotatable in the conveyance direction of the third web 7C, the web position guiding mechanism can reduce friction applied to the third web 7C when the roller mechanism 120 and the third web 7C come in contact with each other. In other words, the work conveying mechanism 100 can prevent excessive load applied to the third web 7C.

According to the present embodiment, the outer side roller 122 has the outer circumferential surface 122S provided in the position corresponding to the end 118 of the adsorbing pad 110, and the outer side roller 124 has the outer circumferential surface 124S provided in the position corresponding to the end 114 of the adsorbing pad 110. In other words, the roller mechanism 120 has shapes further closer to the shapes of the central portion and the outer edge portions of the absorber 4 and can locate the third web 7C. Accordingly, the roller mechanism 120 can cause the third web 7C to be adhered to the absorber 4 more firmly.

According to the present embodiment, the outer side roller 122 and the outer side roller 124 increase their outer diameters of the outer side roller as they toward the outer side of the third web 7C in the width direction. Accordingly, the outer side roller 122 and the outer side roller 124 can steadily locate the outer edge portion of the third web 7C in the width direction on the adsorbing pad 110 side in such a way as to bring the outer edge portion closer to the adsorbing pad 110 at the passing point P2.

According to the present embodiment, the roller mechanism 120 further includes the central roller 126 provided in the position corresponding to the central portion of the adsorbing pad 110. Accordingly, the roller mechanism 120 can locate the third web 7C in accordance with the shape of the central portion and the shapes of the outer edge portions of the absorber 4. Thus, the roller mechanism 120 can cause the third web 7C to be adhered to the absorber 4 more firmly.

According to the present embodiment, since the roller used for the roller mechanism 120 is formed of an elastic member, the roller mechanism 120 can be deformed in accordance with the shape of the absorber 4 when locating the third web 7C. Thereby, the roller mechanism 120 can suppress excessive stress or the like applied to the third web 7C. Since the outer side roller 122 (outer side roller 124) gradually increases its outer diameter toward the outer side of the third web 7C in the width direction, a difference in the circumferential velocity (so-called different circumferential velocity) is produced in the outer side roller 122 (outer side roller 124) depending on the outer diameter. On the other hand, with the roller formed of the elastic member, the different circumferential velocity at the time of transfer can be reduced because of deformation of the elastic member. Consequently, the roller mechanism 120 can further suppress generation of wrinkles and poor transfer.

According to the present embodiment, the roller mechanism 120C is provided closer to the shaft center 104 of the rotation drum 102 than the tangent L1. Accordingly, the roller mechanism 120 can steadily locate the third web 7C on the adsorbing pad 110 side at the passing point P2.

(7) Modified Example

Figure 6:
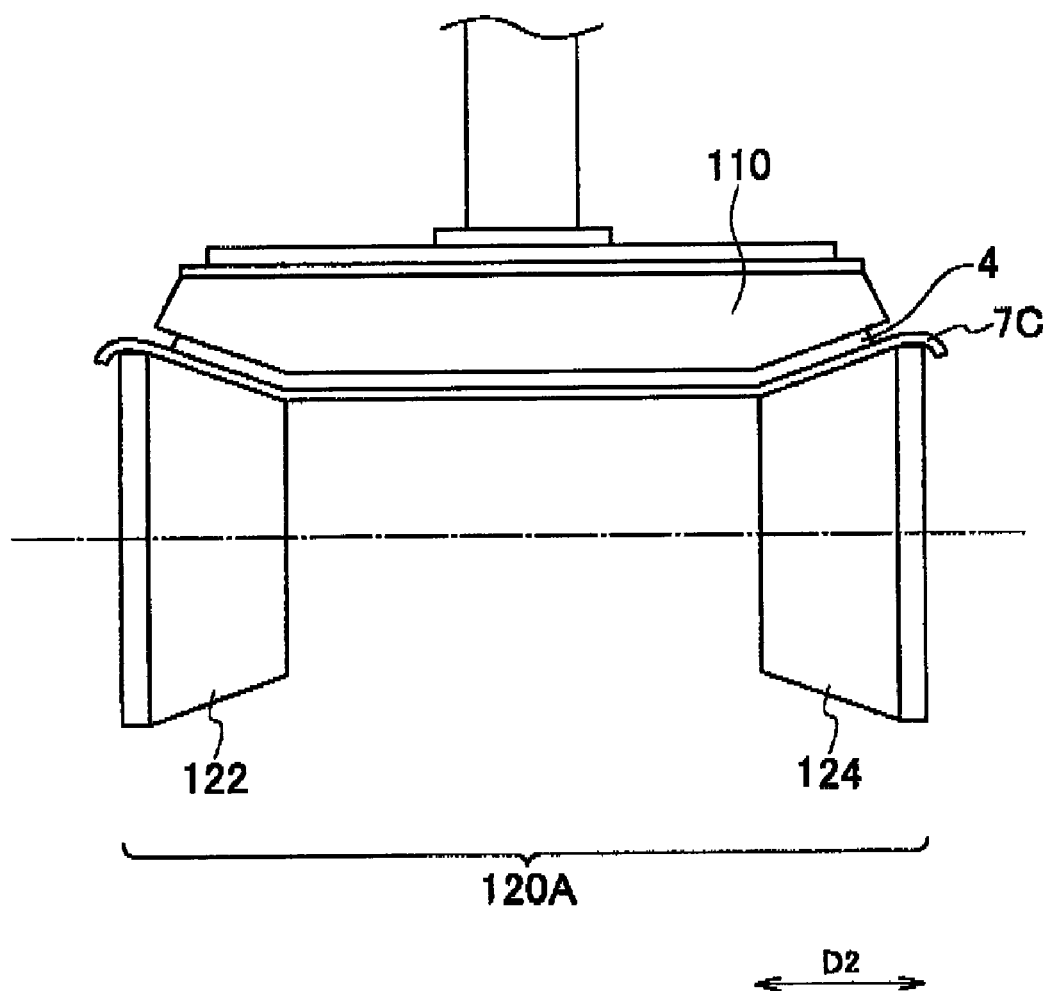
FIG. 6 is a side view showing a web position guiding mechanism according to a modified example of the first present embodiment of the present invention.

The roller mechanism 120 according to the embodiment mentioned above may be modified as follows. Same reference symbols will be given to same parts as those in the roller mechanism 120 according to the embodiment mentioned above, and parts different from those in the embodiment mentioned above will be mainly described using FIG. 6. FIG. 6 is a side view showing a web position guiding mechanism according to a modified example of the present embodiment.

The roller mechanism 120 according to the embodiment mentioned above is formed of the outer side roller 122, the outer side roller 124, and the central roller 126. On the other hand, a roller mechanism 120A according to the modified example does not have the central roller 126, and the roller mechanism 120A is formed of an outer side roller 122 and an outer side roller 124.

Such an outer side roller 122 (outer side roller 124) can securely cause only the outer edge portion of the absorber 4 to adhere to the web, which cannot well adhere to the third web 7C. Since the roller mechanism 120A can prevent occurrence of the different circumferential velocity generated between the central roller and the outer side roller 122 (outer side roller 124), the roller mechanism 120A can prevent twist between the central portion and the outer edge portions of the third web 7C attributed to the different circumferential velocity.

When such a roller mechanism 120A is used, adhesion between the central portion of the third web 7C and the absorber 4 can be strengthened by providing a pressing process to press the whole surfaces of the absorber 4 having its outer edge portion adhering to the third web 7C and the third web 7C downstream of the passing point P2. Therefore, the roller mechanism 120A can cause the work to adhere to the web more securely.

In the roller mechanism 120 according to the embodiment mentioned above, the outer side roller 122, the outer side roller 124, and the central roller 126 share the same shaft center, and are integrally formed. However, the outer side roller 122, the outer side roller 124, and the central roller 126 do not need to be integrally formed. Moreover, each of the outer side roller 122, the outer side roller 124, and the central roller 126 may have an independent shaft center from each other.

With such a roller mechanism, since the shaft centers of the rollers are independent of each other, occurrence of the different circumferential velocity between the rollers can be reduced, compared with the roller mechanism in which the rollers having different outer diameters are integrally formed. Thereby, generation of wrinkles and poor transfer can be further suppressed. Furthermore, in such a roller mechanism, since the shaft centers of the rollers are independent of each other, an arrangement position such as angle adjustment can be adjusted one by one.

The absorber 4 according to the embodiment mentioned above has a fixed thickness, but the thickness is not limited to this. The thickness of the absorber 4 may be varied. For example, when an absorber in the central portion of the absorber 4 is formed thicker, the roller mechanism 120 can also cause the third web 7C to be adhered to the absorber 4 in accordance with the shape of the absorber 4.

Second Embodiment

According to the first embodiment mentioned above, the roller mechanism 120 in the work conveying mechanism 100 is formed to have the same shaft center.

Figure 7:
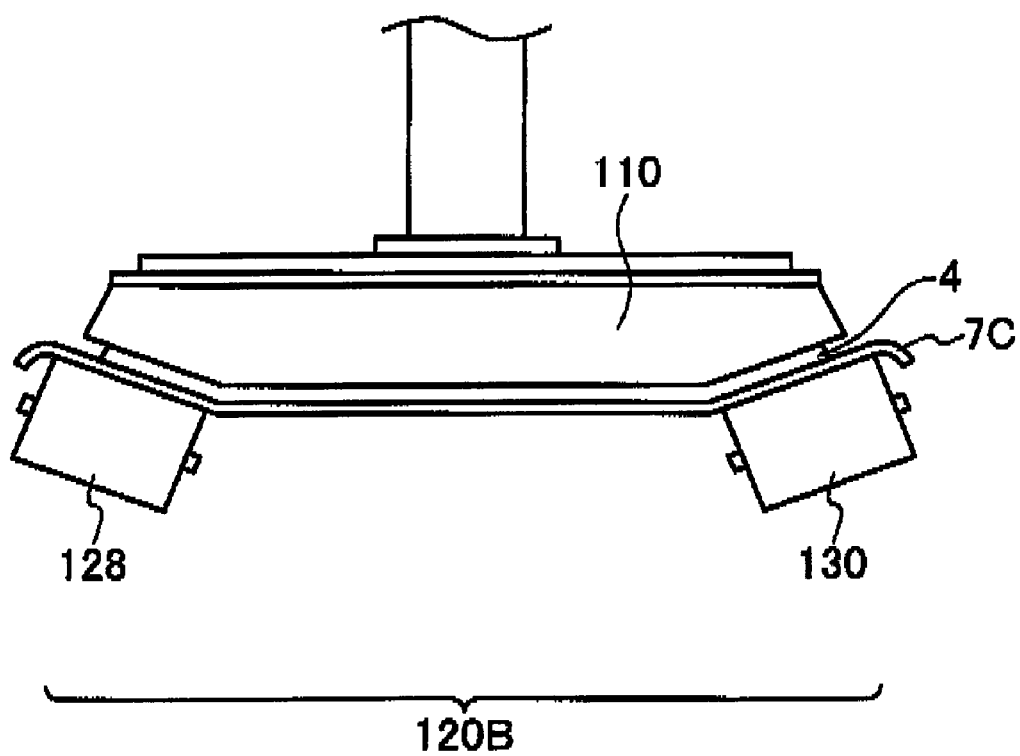
FIG. 7 is a side view showing a web position guiding mechanism according to a second present embodiment of the present invention.

According to a second embodiment, using FIG. 7, description will be given of a configuration including a roller different from that in the roller mechanism 120 of the first embodiment. FIG. 7 is a side view showing a web position guiding mechanism according to the present embodiment.

In the second embodiment below, points different from those in the first embodiment will be mainly described, and duplicated description will be omitted.

In the present embodiment, description will be given of (1) Detailed Configuration of Web Position Guiding Mechanism, (2) Advantages and Effects, and (3) Modified Example.

(1) Detailed Configuration of Web Position Guiding Mechanism

As shown in FIG. 7, a web position guiding mechanism (roller mechanism 120B) in the present embodiment is characterized by including an outer side roller 128 and an outer side roller 130 having shaft centers approximately parallel to a line along the outer edge portion of the adsorbing face. The outer circumferential surfaces of the outer side roller 128 and the outer side roller 130 are approximately parallel to the line along the outer edge portion of the adsorbing face.

(2) Advantages and Effects

As described above, according to the present embodiment, the roller mechanism 120B has the shaft center approximately parallel to the line along the outer edge portion of the adsorbing face. Moreover, the outer circumferential surfaces of the outer side roller 128 and the outer side roller 130 are approximately parallel to the line along the outer edge portion of the adsorbing face. Accordingly, in addition to the effect of the first embodiment, the different circumferential velocity can be prevented from being generated in each roller (outer side roller 128, outer side roller 130). Therefore, the roller mechanism 120B can prevent generation of wrinkles, and can cause the work to adhere to the web.

(3) Modified Example

Figure 8:
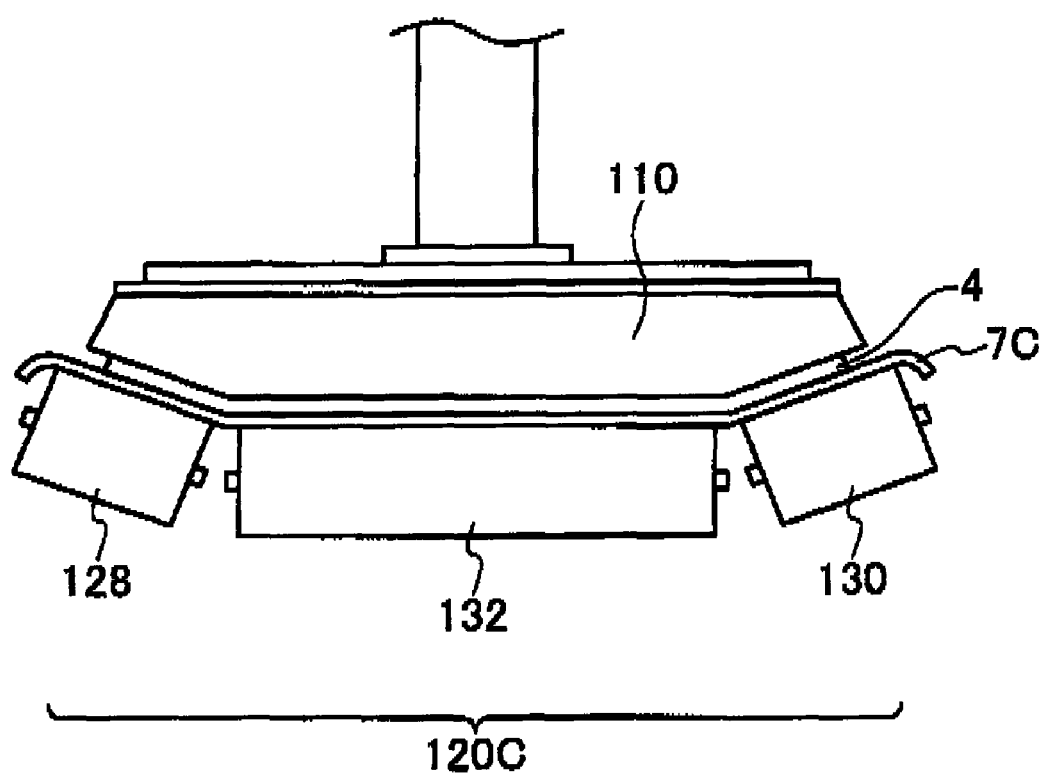
FIG. 8 is a side view showing a web position guiding mechanism according to a modified example of the second present embodiment of the present invention.

The roller mechanism 120B according to the embodiment mentioned above may be modified as follows, as shown in FIG. 8. FIG. 8 is a side view showing a web position guiding mechanism according to a modified example of the present embodiment.

A roller mechanism 120C according to the modified example includes a central roller 132, in addition to the roller mechanism 120B according to the embodiment.

Specifically, the roller mechanism 120C includes the central roller 132 that is provided in a position corresponding to the central portion of the adsorbing part as shown in FIG. 8, and has a shaft center approximately parallel to the width direction of the third web 7C. The outer side roller 128 and the outer side roller 130 are provided on the outer side of the central roller 132 in the width direction of the third web 7C.

With the roller mechanism 120C, the same effects as those in the second embodiment can be obtained, and simultaneously, the central portion of the third web 7C can adhere to the absorber 4 more firmly using the central roller 132.

Third Embodiment

According to the first embodiment and the second embodiment mentioned above, the web position guiding mechanism in the work conveying mechanism 100 is the roller mechanism including the roller.

According to a third embodiment, the web position guiding mechanism in the work conveying mechanism 100 is provided upstream of the passing point P2 in the conveyance direction of the third web 7C.

Figure 9:
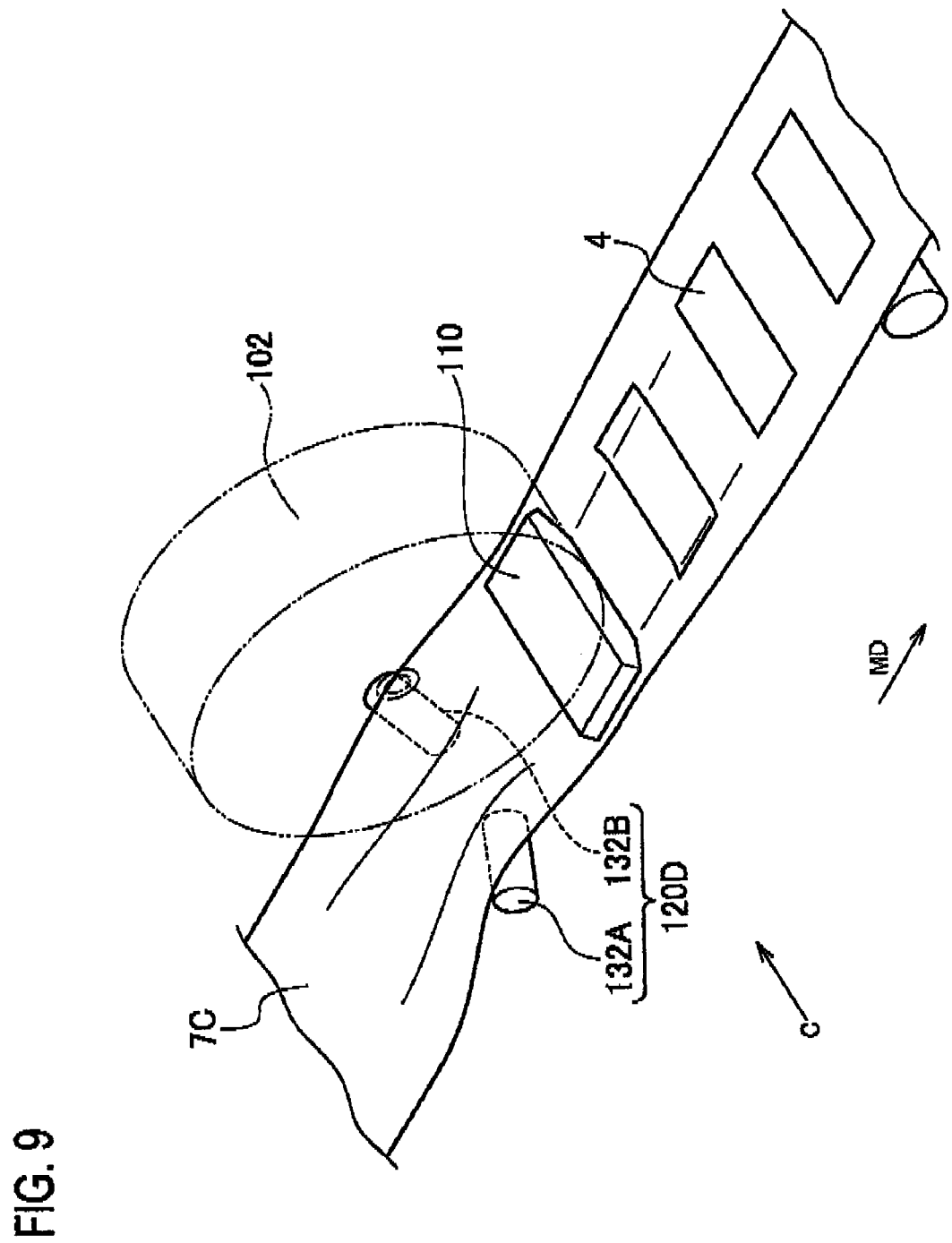
FIG. 9 is a perspective view showing an entire configuration of a manufacturing apparatus of an absorbent article according to a third embodiment of the present invention.
Figure 10:
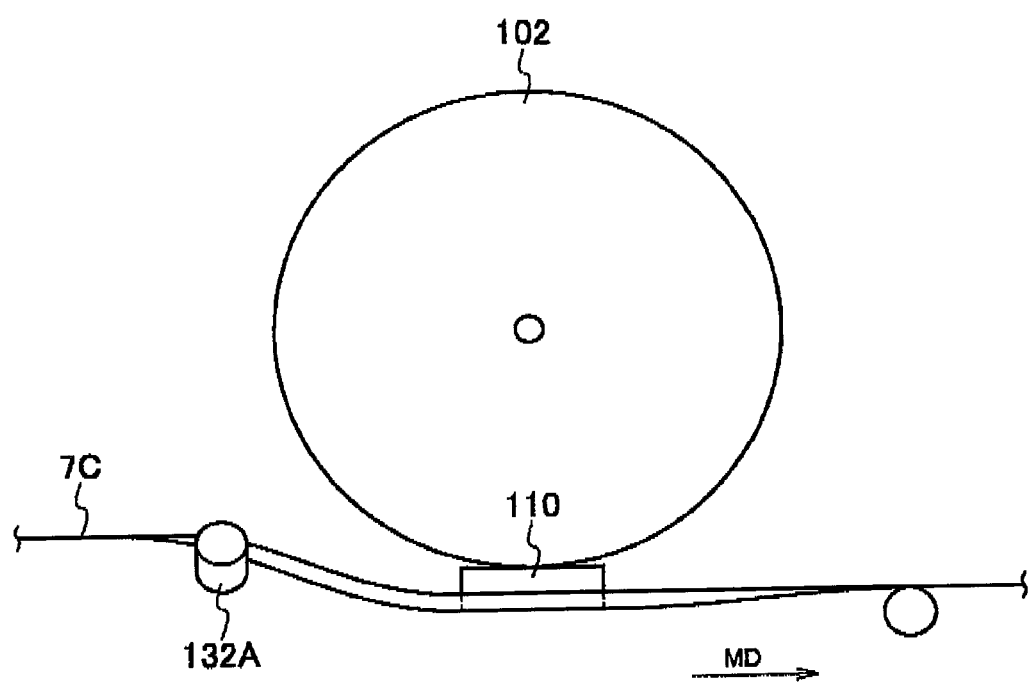
FIG. 10 is a side view (a view seen in the direction of an arrow C in FIG. 9) showing an entire configuration of the manufacturing apparatus of the absorbent article according to the third embodiment of the present invention.

FIG. 9 is a perspective view showing an entire configuration of a manufacturing apparatus of an absorbent article according to the third embodiment of the present invention. FIG. 10 is a side view (a view seen in the direction of an arrow C of FIG. 9) showing the entire configuration of the manufacturing apparatus of the absorbent article according to the third embodiment of the present invention. In the third embodiment below, points different from those in the first embodiment will be mainly described, and duplicated description will be omitted.

In the present embodiment, description will be given of (1) Entire Configuration of Manufacturing Apparatus of Absorbent Article, (2) Advantages and Effects, and (3) Modified Example.

(1) Entire Configuration of Manufacturing Apparatus of Absorbent Article

A web position guiding mechanism 120D in the present embodiment is provided upstream of the passing point P2 in the conveyance direction of the third web 7C. The web position guiding mechanism 120D includes a supporter that supports the outer edge portion of the third web 7C in the width direction.

Specifically, the web position guiding mechanism 120D is formed of a support member 132A and a support member 132B. Using, for example, a turn bar or a cloth guider as the support member 132A and the support member 132B, the outer edge portion of the third web 7C in the width direction can be supported. Alternatively, as the support member 132A and the support member 132B, a roller that rotates in the conveyance direction of the third web 7C may be used.

In a view point from the extending direction of the shaft center 104 of the rotation drum 102, the support member 132A and the support member 132B are provided closer to the shaft center of the rotation drum 102 than the tangent to the rotation trajectory of the center of the adsorbing face 112 at the passing point P2.

(2) Advantages and Effects

According to the present embodiment, since the third web 7C is supported by the support member 132A and the support member 132B, the web position guiding mechanism 120D can bring the outer edge portion of the third web 7C in the width direction closer to the adsorbing pad 110 than the central portion of the third web 7C in the width direction. Consequently, similarly to the advantages and effects of the first embodiment, the web position guiding mechanism 120D can prevent generation of wrinkles and poor transfer, and can cause the work to adhere to the web more securely.

According to the present embodiment, the third web 7C comes in contact with the adsorbing pad 110 of the rotation drum 102 with a force being applied thereto in the conveyance direction MD between the supporters of the support member 132A and the support member 132B, and the passing point P2. Moreover, since the web position guiding mechanism 120D is provided upstream of the passing point P2 in the conveyance direction of the third web 7C, the outer edge portion of the third web 7C in the width direction can be easily brought closer to the adsorbing pad 110 than the central portion of the third web 7C in the width direction.

According to the present embodiment, the web position guiding mechanism 120D can suppress the third web 7C from being deformed at the passing point P2 than the web position guiding mechanism 120 employing the roller does. Accordingly, the web position guiding mechanism 120D is suitable when a web or the like having weak elasticity are used.

(3) Modified Example

The web position guiding mechanism 120D according to the embodiment mentioned above may be modified as follows.

The web position guiding mechanism 120D according to the embodiment mentioned above may support, by using a conveying unit such as a belt conveyor, instead of a turn bar, as the support member 132A and the support member 132B, only the outer edge portion of the third web 7C in the width direction and convey the third web 7C from above the rotation drum 102.

The web position guiding mechanism 120D according to embodiment mentioned above may be provided downstream of the passing point F2 in the conveyance direction of the third web 7C. Thereby, since the third web 7C is soft and easily deformed, the outer edge portion of the third web 7C in the width direction can be brought closer to the adsorbing pad 110 than the central portion of the third web 7C in the width direction.

Other Embodiments

As described above, the content of the present invention has been disclosed through the embodiments of the present invention. However, the descriptions and the drawings constituting a part of the disclosure should not be construed to limit the present invention. Various alternative embodiments, examples, and operational techniques should be apparent to those skilled in the art from this disclosure.

Figure 11:
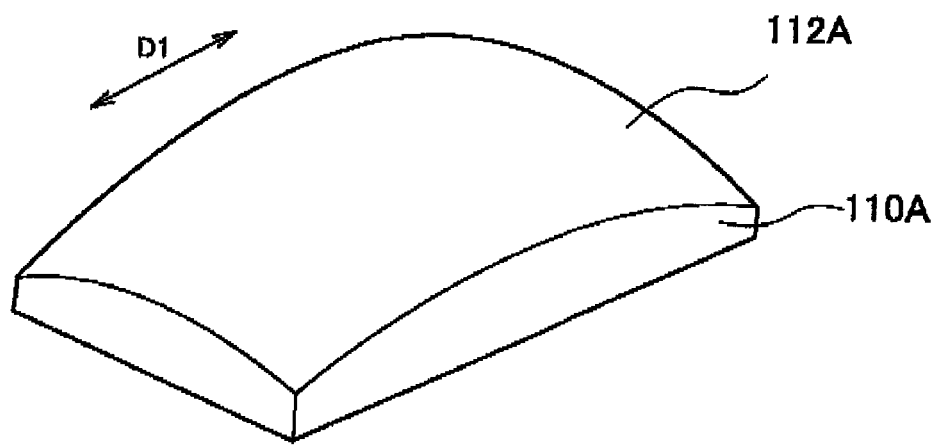
FIG. 11 is a perspective view showing an entire configuration of an adsorbing pad according to other embodiment of the present invention.

For example, as shown in FIG. 11, a shape of an adsorbing face 112A of an adsorbing pad 110A may be formed in a dome-like shape such that the central portion of the adsorbing face 112A protrudes more than the outer edge portion of the adsorbing face 112A does.

Figure 12:
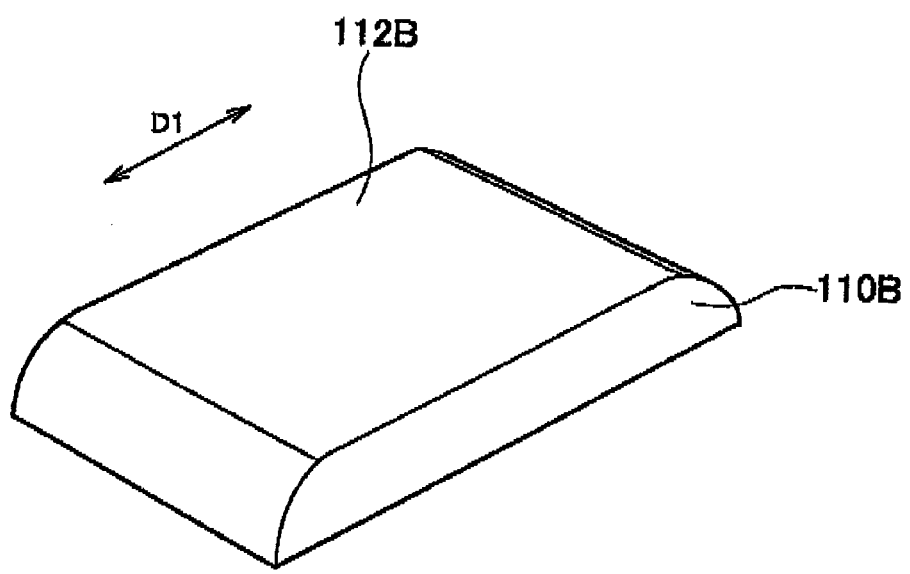
FIG. 12 is a perspective view showing an entire configuration of an adsorbing pad according to a modified example of other embodiment of the present invention.

For example, as shown in FIG. 12, as to a shape of an adsorbing face 112B of an adsorbing pad 110B in a cross section of the adsorbing pad 110B in the first arrangement direction D1, the outer edge portion of the adsorbing face 112B of the adsorbing pad 110B may be formed in a curved surface shape being curved toward the shaft center 104 side of the rotation drum 102.

In this manner, as a matter of course, the present invention includes various embodiments which are not described herein. Accordingly, the technical scope of the present invention is defined only by the particular matters contained in the scope of claims which is appropriate from this disclosure.

What is claimed is:

1. An apparatus for manufacturing an absorbent article, comprising:
    a rotation drum rotatable about a shaft center and having an adsorbing part for adsorbing a work, which is a component forming a part of the absorbent article, at a receiving point, said rotation drum configured to change an arrangement direction of the work from a first arrangement direction of the work to a second arrangement direction of the work at a passing point wherein the work to be passed onto a web while the rotation drum is rotating; and
    a web position guiding mechanism provided below and opposite the rotation drum at the passing point, and configured to locate the web on the adsorbing part,
    wherein
    the adsorbing part has a central portion and two outer portions extending, at the passing point, upwardly and obliquely relative to the central portion,
    said web position guiding mechanism has outer portions that are separate from each other and extend obliquely upwardly and correspondingly to the outer portions of the adsorbing part, respectively, so that the web has opposite outer edge portions in a width direction of the web which correspond to the outer portions of the web position guiding mechanism and which are closer to the shaft center of the rotation drum than a central portion of the web in the width direction,
    the web position guiding mechanism is a roller mechanism that is rotatable in a conveyance direction of the web perpendicular to the width direction of the web,
    the roller mechanism includes an outer side roller extending, at the passing point, upwardly, obliquely, and correspondingly to one of the outer portions of the adsorbing part,
    the roller mechanism further includes another outer side roller extending, at the passing point, upwardly, obliquely, and correspondingly to the other one of the outer portions of the adsorbing part, and
    the outer side rollers are spaced by a central space corresponding to the central portion of the adsorbing part whereby the central portion of the web is unsupported when the central portion of the adsorbing part presses the web.

2. The apparatus according to claim 1, wherein the outer portions of the adsorbing part are oblique toward the shaft center of the rotation drum.

3. The apparatus according to claim 1, wherein the outer side roller is rotatable about a shaft center which is approximately parallel to the corresponding outer portion of the adsorbing part.

4. The apparatus according to claim 1, wherein the outer side roller of the roller mechanism includes an elastic member.

5. An apparatus for manufacturing an absorbent article, comprising:
    a rotation drum rotatable about a shaft center and having an adsorbing part for adsorbing a work, which is a component forming a part of the absorbent article, at a receiving point, said rotation drum configured to change an arrangement direction of the work from a first arrangement direction of the work to a second arrangement direction of the work at a passing point wherein the work to be passed onto a web while the rotation drum is rotating;
    a web position guiding mechanism provided below the rotation drum and configured to locate the web on the adsorbing part,
    wherein
    the adsorbing part has a central portion and two outer portions extending, at the passing point, upwardly and obliquely relative to the central portion,
    the web position guiding mechanism includes a support member for supporting the web, said support member has outer portions that are separate from each other and extend obliquely upwardly, so that the web has opposite outer edge portions in a width direction of the web which correspond to the outer portions of the support member and which are closer to the shaft center of the rotation drum than a central portion of the web in the width direction,
    the support member is a roller mechanism that is rotatable in a conveyance direction of the web perpendicular to the width direction of the web,
    the roller mechanism includes an outer side roller extending, at the passing point, upwardly, obliquely, and correspondingly to one of the outer portions of the adsorbing part,
    the roller mechanism further includes another outer side roller extending, at the passing point, upwardly, obliquely, and correspondingly to the other one of the outer portions of the adsorbing part, and
    the outer side rollers are spaced by a central space corresponding to the central portion of the adsorbing part whereby the central portion of the web is unsupported when the central portion of the adsorbing part presses the web.

6. An apparatus for manufacturing an absorbent article, comprising:
- a rotation drum rotatable about a shaft center and having an adsorbing part for adsorbing a work, which is a component forming a part of the absorbent article, at a receiving point, said rotation drum configured to change an arrangement direction of the work from a first arrangement direction of the work to a second arrangement direction of the work at a passing point wherein the work to be passed onto a web while the rotation drum is rotating;
- a web position guiding mechanism provided below and opposite the rotation drum at the passing point, and configured to locate the web on the adsorbing part, wherein
- the adsorbing part has a central portion and two outer portions extending, at the passing point, upwardly and obliquely relative to the central portion,
- said web position guiding mechanism has outer portions that are separate from each other and extend obliquely, away from the work on the web, and correspondingly to the outer portions of the adsorbing part, respectively, so that the web has an outer edge portion in a width direction of the web which corresponds to one of the outer portions of the web position guiding mechanism and is closer to the shaft center of the rotation drum than a central portion of the web in the width direction,
- said web position guiding mechanism is a roller mechanism that is rotatable in a conveyance direction of the web perpendicular to the width direction of the web,
- the roller mechanism includes outer side rollers extending, at the passing point, upwardly, obliquely, and correspondingly to the outer portions of the adsorbing part, respectively, and
- the outer side rollers are spaced by a central space corresponding to the central portion of the adsorbing part whereby the central portion of the web is unsupported when the central portion of the adsorbing part presses the web.

7. The apparatus according to claim 6, wherein each of said outer side rollers has inclined conical surfaces.

8. The apparatus according to claim 6, wherein axes of the outer side rollers are coincident.

9. The apparatus according to claim 6, wherein axes of the outer side rollers are inclined relative to each other.

10. The apparatus according to claim 6, wherein said web position guiding mechanism is upstream of the rotation drum in a conveyance direction of the web perpendicular to the width direction of the web.

* * * * *